(12) United States Patent
Timberlake et al.

(10) Patent No.: US 7,202,311 B2
(45) Date of Patent: Apr. 10, 2007

(54) PHOSPHINE OXIDE HYDROXYARL MIXTURES WITH NOVOLAC RESINS FOR CO-CURING EPOXY RESINS

(75) Inventors: Larry D. Timberlake, West Lafayette, IN (US); Mark V. Hanson, West Lafayette, IN (US); E. Bradley Edwards, Lafayette, IN (US)

(73) Assignee: Great Lakes Corporation, West Bend, IN (US)

( * ) Notice: Subject to any disclaimer, the term of this patent is extended or adjusted under 35 U.S.C. 154(b) by 461 days.

(21) Appl. No.: 10/866,882

(22) Filed: Jun. 14, 2004

(65) Prior Publication Data

US 2004/0225080 A1 Nov. 11, 2004

Related U.S. Application Data

(60) Division of application No. 10/317,587, filed on Dec. 12, 2002, now Pat. No. 6,887,950, which is a continuation-in-part of application No. 10/077,701, filed on Feb. 14, 2002, now Pat. No. 6,733,698.

(60) Provisional application No. 60/268,975, filed on Feb. 15, 2001.

(51) Int. Cl.
- B32B 27/04 (2006.01)
- C08F 9/53 (2006.01)
- C08G 59/06 (2006.01)
- C08K 21/12 (2006.01)

(52) U.S. Cl. .................. 525/480; 252/609; 428/297.4; 428/413; 428/418; 525/523; 525/485; 528/398; 549/219; 568/17

(58) Field of Classification Search ...................... None
See application file for complete search history.

(56) References Cited

U.S. PATENT DOCUMENTS

| | | | |
|---|---|---|---|
| 3,676,393 A | 7/1972 | Pilrma | 260/45.7 P |
| 3,751,481 A | 8/1973 | Weinberg | 260/601.5 P |
| 3,784,638 A | 1/1974 | Lambert | 260/526 S |
| 3,852,362 A | 12/1974 | Lambert | 260/606.5 P |
| 4,211,687 A | 7/1980 | Salee | 260/40 R |
| 4,221,694 A | 9/1980 | Salee | 260/40 R |
| 4,251,429 A | 2/1981 | Salee | 260/40 R |
| 4,256,625 A | 3/1981 | Dachs | 260/40 R |
| 4,345,059 A | 8/1982 | Fretz, Jr. et al. | 528/102 |
| 4,444,960 A | 4/1984 | Salee et al. | 525/534 |
| 4,866,155 A | 9/1989 | Mueller et al. | 528/191 |
| 4,973,631 A | 11/1990 | McGrath et al. | 525/534 |
| 5,376,453 A | 12/1994 | von Gentzkow et al. | 428/415 |
| 5,399,654 A | 3/1995 | Ko et al. | 528/99 |
| 5,458,978 A | 10/1995 | Bottcher et al. | 428/413 |
| 5,508,462 A | 4/1996 | Bright et al. | 558/99 |
| 5,576,357 A | 11/1996 | Bayer et al. | 522/170 |
| 5,587,243 A | 12/1996 | von Gentzkow et al. | 428/413 |
| 5,648,171 A | 7/1997 | von Gentzkow et al. | 428/413 |
| 6,097,100 A | 8/2000 | Eguchi et al. | 257/787 |
| 6,177,489 B1 | 1/2001 | Okuse et al. | 523/451 |
| 6,403,220 B1 | 6/2002 | Brennan et al. | 428/413 |

FOREIGN PATENT DOCUMENTS

| | | |
|---|---|---|
| DE | 2 254 902 | 5/1973 |
| DE | 3510416 A1 | 9/1986 |
| EP | 0 412 425 B1 | 1/1996 |
| EP | 0 795 570 A1 | 9/1997 |
| EP | 1 116 774 A2 | 7/2001 |
| JP | 61-134395 | 6/1986 |
| JP | 5-57991 | 8/1993 |
| JP | 200-186186 | 7/2000 |
| RU | 620491 A | 7/1978 |
| WO | WO 99/00451 | 1/1999 |
| WO | WO 01/42253 | 6/2001 |
| WO | WO 01/42359 | 6/2001 |

OTHER PUBLICATIONS

"Ir Spectra of the Oxides and Sulphides of Triarylphosphines and Triarylarsines", V. Baliah et al., J. Indian Chem. Soc., vol. 67, May 1990, pp. 430-431; "Synthesis and Solid-State Structures of Substituted Arylphosphine Oxides", Craig M. Whitaker et al., J. Org. Chem. 1995, 60, 3499-3508; "Derivatives of Triphenylphosphine and Triphenylphosphine Oxide", Allen E. Senear et al.,J.Org.Chem. 1960, 25(10), pp. 2001-2006.

"Synthesis and Characterization of Epoxy-Novolac Composite-Steel Adhesives", M.B. Bump et al., Polymer Materials Science & Engineering, V83, 2000, pp. 19-20; "The Mass Spectra of Some para Substituted Triarylphosphines and Triarylphosphine Oxides", G. Marshall, Organic Mass Spectrometry, vol. 16, No. 6, 1981, pp. 272-274.

"N-Phenyl-P,P,P-triarylphospha-?5-azenes, Triaarylphosphines, and Triarylphosphine Oxides. Substituent Effects on 15N, 31P, and 13C NMR Spectra", of W-N Chou et al., J. Org. Chem. 1991, 56, pp. 2762-2769; "Synthesis and Characterization of Phosphine Oxide Diol Modified Epoxy Adhesives", M.A. Hickner et al., Polymer Preprints 2000, 412, pp. 1372-1373; Synthesis and Flammability of Copoly(isophthalamide)s. II. With Pendant Phosphorus Groups, K.G. Gravalos, Journal of Polymer Science: Part A: Polymer Chemistry, vol. 31, 1993, pp. 1355-1364.

(Continued)

Primary Examiner—Robert Sellers
(74) Attorney, Agent, or Firm—Daniel Reitenbach

(57) ABSTRACT

There is disclosed a novel mixture of polyhydroxy phenolic curing agents, such as novolac resins blended with a mixture of mono, bis and tris hydroxyaryl phosphine oxides for co-curing epoxy resins and imparting flame resistance thereto. A preferred composition includes a mixture of monohydroxyaryl, bishydroxyaryl and trishydroxyaryl phosphine oxide and a benzoguanamine/phenol/formaldehyde terpolymer which is used along with an epoxy resin to produce flame-resistant printed wiring boards without the use of halogens.

14 Claims, 1 Drawing Sheet

OTHER PUBLICATIONS

"NMR Spectral Data: A Compilation of Aromatic Proton Chemical Shifts in Mono- and Di-Substituted Benzenes", B.L. Shapiro et al., J. Phys. Chem. Ref. Data, vol. 6, No. 3, 1977, pp. 919-991; "Sn-Zn System Lead Free Solder Paste", Japan Printed Circuit Association, Apr. 2001, pp. 1-18.

"Phosphorus-Containing Epoxy for Flame Retardant. I. Synthesis, Thermal, and Flame-Retardant Properties", Y-L Liu et al., Journal of Applied Polymer Science, vol. 61, 1996, pp. 613-621; "Intumescent Fire Retardant Epoxy Resins", G. Camino, Chemistry and Technology of Polymer Additives, Chapter 7, 1999, pp. 108-134.

"Chemical Modification of Epoxy Resins by Dialkyl (or Aryl) Phosphates: Evaluation of Fire Behavior and Thermal Stability", D. Derouet et al., Journal of Applied Polymer Science, vol. 62, 1996, pp. 1855-1868; "Syntheses, Structure, Reactivity, and Thermal Properties of New Cyclic Phosphine Oxide Epoxy Resins Cured by Diamines", M-D Shau et al., Journal of Polymer Science: Part A: Polymer Chemistry, vol. 34, 1996, pp. 387-396.

"Structure Characterization, Reactivity, and Thermal Properties of New Cyclic Phosphine Oxide Epoxy Resin Containing Tetra-Oxirane Rings", M-D Shau et al., Journal of Applied Polymer Science, vol. 68, 1998, pp. 1397-1409; "Synthesis, Characterization, and Polymerization Reactions of Abx Triarylphospine Oxide Monomers", E. Fossum, Polymer Preprints 2000, 41(1), pp. 200-201.

"Self-extinguishing Epoxy Resins without Flame Retardants: Their Potential Use in Electronics", Y. Kiuchi et al., The 12th Annual BCC Conference on Flame Retardancy, Recent Advances in Flame Retardancy of Polymeric Materials, May 21-23, 2001; "Synthesis, Characterization, Thermal, and Flame Retardant Properties of Phosphate-Based Epoxy Resins", Y-L Liu et al., John Wiley & Sons, Inc., 1997, pp. 565-574.

Copper-Clad Laminates for Use as Printed Circuit Boards, M. Perry et al., Plastics and Resisn Compositions, Royal Society of Chemistry, 1995, pp. 74-99; and "Nucleophotic Constants of Diphenyl P", Teoreticheskeye I eksperimental'naya Khimiia, v. 3(6), 1967, pp. 824-829.

PHOSPHINE OXIDE HYDROXYARL MIXTURES WITH NOVOLAC RESINS FOR CO-CURING EPOXY RESINS

CLAIM FOR PRIORITY

This application is a divisional patent application of U.S. patent application Ser. No. 10/317,587, Dec. 12, 2002 U.S. Pat. No. 6,887,950 which application is a continuation-in-part of U.S. patent application Ser. No. 10/077,701, filed Feb. 14, 2002, entitled "Novel Hydroxyaryl Phosphine Oxides, Glycidyl Ethers and Epoxy Compositions, Composites and Laminates Derived Therefrom" U.S. Pat. No. 6,733, 698. U.S. Ser. No. 10/077,701 was based on U.S. Provisional Patent Application Ser. No. 60/268,975, filed Feb. 15, 2001, entitled "Mixed Hydroxyphenyl Phosphine Oxides and Glycidyl Ethers and Epoxy Oligomers Derived Therefrom for Flame Retarding Printed Wiring Boards". The priorities of the foregoing applications are hereby claimed.

FIELD OF THE INVENTION

The present invention relates generally to the formulation and use of mixtures of hydroxyaryl phosphine oxides and polyhydroxy compounds such as novolac resins as co-curing agents for epoxy resins with enhanced flame retardant properties. The hydroxyaryl phosphine oxide/novolac resin co-curing agents are suitable for flame retarding printed wiring boards. More particularly, the invention is directed to using these co-curing agents in epoxy resin systems to prepare prepregs, laminates, particularly copper-clad laminates, useful in manufacturing electronic components without the use of halogen-containing compounds.

BACKGROUND OF THE INVENTION

Composite materials based on epoxy resins have been used in a variety of day-to-day applications for a long time and continue to have considerable importance because of their versatility. A specific example of such an application includes but is not limited to electrical laminates used in printed circuit boards (printed wiring boards, PWB). The epoxy resins used therein have particularly gained popularity because of their ease of processibility. Those epoxy resins also feature good mechanical and chemical properties, such as for example, toughness and resistance to a variety of organic solvents and also display good chemical and moisture resistance. These properties permit the epoxy resin materials to be adapted to diverse application purposes and allow the materials sharing in the composite to be used advantageously.

Generally, the epoxy resins are readily processed into composite materials for PWB applications via the manufacturing of prepregs (B-staging). For example, the substrate material, which is typically an inorganic or organic reinforcing agent in the form of fibers, fleece and fabric or textile materials, is impregnated with the resin. This may be accomplished by coating the substrate with a resin solution in an easily vaporizable or volatilizable solvent. The coating may be carried out by a variety of well-known techniques including rolling, dipping, spraying, and combinations thereof. The prepregs are then heated in an oven chamber to remove solvent and to partially cure the resin. The prepregs obtained after this process must not self-adhere, but they also should not be fully cured. In addition, the prepregs must be sufficiently stable in storage. In the subsequent processing into composite materials, the prepregs must furthermore fuse when there is a rise in temperature and pressure and must bind together under pressure with the reinforcing agents or insertion components as well as with the materials provided for the composite as compactly and permanently as possible; that is the cross-linked epoxy resin matrix must form a high degree of interfacial adherence with the reinforcing agents, as well as with the materials to be bonded together, such as metallic, ceramic, mineral and organic materials.

A key requirement in many applications is the requirement for flame resistance. In many areas, this requirement is given first priority, due to the danger to human beings and material assets, for example in structural materials for airplane and motor vehicle construction and for public transportation vehicles. In electrotechnical and particularly electronic applications, it is absolutely necessary for the electrical laminate materials to be flame resistant, due to the substantial worth of the electronic components assembled thereon and the intrinsic value of human life associated with working on or near devices containing PWB components.

Accordingly, it has been customary in the preparation of epoxy-containing laminates to incorporate into the epoxy resin compositions various additives and/or reactives to improve the flame retardancy of the resulting laminate. Many types of flame retardant substances have been used, however, the most common thus far used commercially have been halogen containing compounds such as tetrabromobisphenol A. This material is typically incorporated into an epoxy resin by reaction with the diglycidyl ether of bisphenol A. Typically, in order to reach the desired fire retardancy level (V-0 in the standard "Underwriters Laboratory" test method UL 94), levels of such bromine-containing flame retardant substances are required that provide a bromine content from 10 weight percent to 25 weight percent based on the total weight in the product.

Generally, halogen-containing fire retardant epoxy resins such as those containing tetrabromobisphenol A are considered to be safe and effective. However, there has been increasing interest by some to utilize flame-retarded epoxy systems that are not based on halogen chemistry. It is desirable for these new materials to be able to meet the requirements of fire retardancy and to display the same advantages of mechanical properties, toughness, and solvent and moisture resistance that is offered with the halogenated materials currently used.

One such approach proposed by many researchers has been the use of phosphorus based fire retardants. See for example, EP 0 384 939; EP 0 384 940; EP 0 408 990; DE 4 308 185; DE 4 308 187; WO 96/07685; WO 96/07686; U.S. Pat. Nos. 5,648,171; 5,587,243; 5,576,357; 5,458,978; and 5,376,453; all of which are incorporated herein by reference in their entirety. In all of these references, a formulation is formed from the reaction of a flame retardant derived from a phosphorus compound and an epoxy resin, which is then cured with an amino cross-linker such as dicyandiamide, sulfanilamide, or some other nitrogen element containing cross-linker to form the thermosetting polymer network.

Specific examples of commercially available phosphorus-based fire retardant additives include Antiblaze™ 1045 (Albright and Wilson Ltd, United Kingdom) which is a phosphonic acid ester. Phosphoric acid esters have also been used as additives, such as, for example, PX-200 (Diahachi, Japan). Commercially available reactive phosphorus containing compounds that have been disclosed as being suitable for epoxy resins include Sanko HCA and Sanko HCA-HQ (Sanko Chemical Co., Ltd., Japan)."

Alkyl and aryl substituted phosphonic acid esters have also been used to flame retard epoxy resins. More particularly, $C_1$–$C_4$ alkyl esters of phosphonic acid are of value because they contain a high proportion of phosphorus, and are thus able to impart fire retardant properties upon resins in which they are incorporated. However, the phosphonic acid esters are not satisfactory as a substitute for halogenated flame retardants in epoxy resins for the production of electrical laminates for various reasons. First and foremost of these reasons are the phosphonic acid esters often times impart undesirable properties. For example, the phosphonic acid esters are known plasticizers and thus the laminates formed therefrom tend to exhibit undesirable low glass transition temperatures ($T_g$). An additional drawback is that the use of phosphonic acid esters in amounts sufficient to provide the necessary flame retardancy increases the tendency of the resulting cured epoxy resin to absorb moisture. The moisture absorbency of the cured laminate board is very significant, because laminates containing high levels of moisture tend to blister and fail, when introduced to a bath of liquid solder at temperatures around 260° C., a typical step in the manufacture of printed wiring boards.

Various other phosphorus based flame retardant materials are described in the literature, which are either too expensive or feature certain inferior properties. For example, EP 0 754 728 discloses a cyclic phosphonate as a flame retardant material, which is incorporated into an epoxy resin. However, EP 0 754 728 indicates that this cyclic phosphonate should be present in large quantities, such as in excess of 18 weight percent, in order for the resin system to meet UL 94 V-0. This loading for a phosphonate compound may lead to a depression of the Tg or higher moisture absorption. EP 1 116 774 utilizes a hydrogen phosphinate, 9,10-dihydro-9-oxa-10-phosphaphenanthrene-10-oxide, in conjunction with triphenylphosphine oxide. However, the epoxy resin base requires the use of non-standard epoxy resins; namely a xylene-modified novolac resin and naphthylene aralkyl and biphenyl-modified epoxy resins. WO 99/00451 discloses another flame retardant composition utilizing phosphonic acid esters. Although this composition appears to exhibit improved flame retardant properties at low levels of phosphonic acid ester, there is still a need in the industry for a flame retardant epoxy resin with improved $T_g$ and flame retardant properties. Phosphorus flame retardant additives, in general, can lead to a significant plastisizing effect (U.S. Pat. No. 5,587,243 and references cited therein). Also, in the case of additive compounds, there may be a question of the additives leaching from a thermoset polymer network under processing conditions or over time.

Other methods to impart flame retardancy involve preparation of halogen-free flame retardant epoxy resin compositions using a combination of resinous materials and an inorganic filler, such as aluminum trihydrate (EP 0 795 570 A1) or magnesium hydroxide (JP 2001213980 A2). These materials may, depending on the physical properties, render the processing of the epoxy resins more difficult, as they are insoluble in the resin systems. Additionally, fairly large load levels can be required, which can detract from the properties. See, generally, U.S. Pat. No. 6,097,100 and references cited therein for a description of various inorganic fillers and WO 01/42359.

Phosphorous compounds containing a high number of P—C bonds with a low or no number of P—O bonds have been recognized as having improved hydrolytic and thermal stability properties relative to the materials containing more P—O bonds. These types of phosphorus compounds have also been used to prepare halogen-free flame retardant epoxy resins useful in the manufacture of composite materials. For example, the use of phosphorus-carbon bonded moieties, such as phosphine oxides, have been disclosed in WO 01/42253; U.S. Pat. No. 4,345,059; EP 1 116 774; and JP2000186186, all of which are incorporated herein by reference in their entirety. A key disadvantage of these compositions, however, is that they are costly to prepare, because they utilize unique raw materials. For example, JP2000186186 discloses the use of pure bis(p-hydroxyphenyl)phenyl-phosphine oxide, which requires the use of a pure dichlorophenyl phosphine. In an analogous manner, the phosphine oxides utilized in WO 01/42253 require lithium reagents and cryogenic reaction conditions, thus warranting special equipment for its manufacture. The phosphine oxides display benefits of improved resistance to moisture uptake when compared with other phosphorus compounds that contain P—O bonded moieties, as disclosed in WO 01/42253. See also, U.S. Pat. No. 6,403,220 of Brennan et al.

Thus, it is an object of this invention to provide economical yet useful hydroxyarylphosphine oxide/phenolic compositions for curing epoxy resins having utility in the manufacture of composite materials, such as electrical laminates for printed wiring boards or printed circuit boards.

It is yet an other object of this invention to provide hydroxyarylphosphine oxide containing, hydrolytically and thermally stable, non-halogenated, flame resistant novolac resin mixtures, which are used as curing agents for epoxy resins for making laminates for printed wiring boards and various other composite materials.

Further, it is also an object of this invention to provide hydroxyaryl phosphine oxide/phenolic resin mixtures for curing epoxy resin compositions having improved flammability properties at reduced phosphorous content when compared with phosphine oxide cured epoxy laminates.

A still yet further object of this invention to provide halogen free phosphine oxide/novolac resin containing epoxy resin compositions that are useful as replacements for tetrabromobisphenol A in FR-4 laminate applications.

These and other objects and advantages of the invention will be seen from the following detailed description.

SUMMARY OF THE INVENTION

This invention pertains, in part, to blends derived from a mixture of hydroxylated aromatic phosphine oxides and a co-crosslinking composition provided with a phenolic component having a hydroxy functionality of two or more. The described blends are effective as epoxy resin hardeners which impart flame resistance, high thermal stability, and high moisture resistance to a cured epoxy resin matrix. This invention is thus generally directed to the flame retardation of epoxy resin compositions, more specifically to flame resistant epoxy resins used to prepare prepregs, laminates, and particularly copper clad laminates useful in manufacturing electronic components such as printed wiring boards without the use of halogen-containing compounds.

There is provided in one aspect of the invention a polyhydroxy mixture for co-curing an epoxy resin and imparting flame resistance including a mixture of phosphine oxides including hydroxyaryl phosphine oxides of the formulae:

a mono(hydroxyaryl)phosphine oxide of the formula:

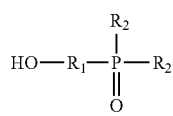

(I)

wherein $R_1$ is a divalent, substituted or unsubstituted arylene moiety and $R_2$ is a monovalent, substituted or unsubstituted aryl moiety or is an alkyl moiety or is an aralkyl moiety; and a bis(hydroxyaryl)phosphine oxide of the formula:

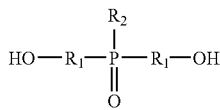

(II)

wherein $R_1$ and $R_2$ are defined as above; and
a tris(hydroxyaryl)phosphine oxide of the formula:

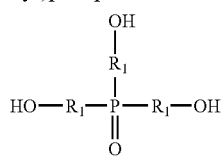

(III)

wherein $R_1$ is defined as above; and
optionally containing minor amounts of a pentavalent phosphine oxide of the formula:

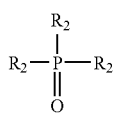

(IV)

wherein $R_2$ is defined as above and the polyhydroxy mixture further includes a phenolic co-crosslinking composition including a phenolic component having a hydroxy functionality of two or more.

As used herein, the term "arylene" refers to a divalent aromatic substituent radicals covalently bonded to the phosphorous atom by way of an aromatic carbon including phenylene, biphenylene, naphthylene, and the like; the term "aryl" refers to corresponding monovalent aromatic substituent radicals covalently bonded to the phosphorous atom by way of an aromatic carbon including phenyl, biphenyl, naphthyl, and the like; substituted analogs thereof means said arylene moiety or aryl moiety is substituted by at least one suitable substituent group selected from the group consisting of straight or branched alkoxy group such as methoxy, straight or branched alkyl such as methyl, alkenyl group such as vinyl, and the like, provided that such substituent does not interfere with the ability of the phosphorus compound to react with the epoxy resin. Thus, for example, when $R_1$ is phenylene, examples of suitable substituted $R_1$ are o, m or p-hydroxy-methyl-phenyl or commonly known as o-cresyl, m-cresyl, or p-cresyl; and so forth.

"Alkyl" means a straight chain, branched or cyclic saturated substituent typically of 1–20 carbon atoms including methyl, ethyl, propyl substituents and so forth; whereas "aralkyl" and like substituents are characterized by bonding to the nucleus through a saturated carbon and including aromatic structures. Such substituents include phenylpropyl or phenylbutyl substituents and so forth.

Preferably the phosphine oxide mixture consists essentially of diphenyl(4-hydroxyphenyl)phosphine oxide, bis(4-hydroxyphenyl)phenylphosphine oxide and tris(4-hydroxyphenyl)phosphine oxide, optionally including minor amounts of triphenylphosphine oxide. The phosphine oxide mixture may consist essentially of bis(4-methylphenyl)(4-hydroxyphenyl)phosphine oxide, bis(4-hydroxyphenyl)(4-methylphenyl)phosphine oxide and tris(4-hydroxyphenyl) phosphine oxide, and optionally include minor amounts of tris(4-methylphenyl)phosphine oxide.

In some cases the phosphine oxide mixture consists essentially of bis(1-naphthyl)(4-hydroxyphenyl)phosphine oxide, bis(4-hydroxyphenyl)(1-naphthyl)-phosphine oxide and tris(4-hydroxyphenyl)-phosphine oxide, optionally including minor amounts of tris(1-naphthyl)-phosphine oxide; or the phosphine oxide mixture consists essentially of bis(2-naphthyl)(4-hydroxyphenyl)phosphine oxide, bis(4-hydroxyphenyl)(2-naphthyl)phosphine oxide and tris(4-hydroxyphenyl)-phosphine oxide, optionally including minor amounts of tris(2-naphthyl)-phosphine oxide. In still yet other embodiments the phosphine oxide mixture consists essentially of bis(4-phenoxyphenyl)(4-hydroxyphenyl) phosphine oxide, bis(4-hydroxyphenyl)(4-phenoxyphenyl) phosphine oxide and tris(4-hydroxyphenyl)-phosphine oxide, optionally including minor amounts of tris(4-phenoxyphenyl)-phosphine oxide or the phosphine oxide mixture consists essentially of bis(2,4,5-trimethylphenyl)(4-hydroxyphenyl)phosphine oxide, bis(4-hydroxyphenyl)(2,4,5-trimethylphenyl)phosphine oxide and tris(4-hydroxyphenyl) phosphine oxide, optionally including minor amounts of tris(2,4,5-trimethylphenyl)phosphine oxide. Additional embodiments include those in which the phosphine oxide mixture consists essentially of bis(tert-butyl)(4-hydroxyphenyl)phosphine oxide, bis(4-hydroxy-phenyl)(tert-butyl) phosphine oxide and tris(4-hydroxyphenyl)-phosphine oxide, optionally including minor amounts of tris(tert-butyl) phosphine oxide.

Generally speaking, the phosphine oxide mixture comprises from about 5 to about 40 mole percent of the mono (hydroxyaryl)phosphine oxide of the formula (I), from about 5 to about 60 mole percent of the bis(hydroxyaryl)phosphine oxide of the formula (II), from about 10 to 90 mole percent of the tris(hydroxyaryl)phosphine oxide of the formula (III) and from about 0 up to about 10 mole percent of the pentavalent phosphine oxide of the formula (IV), based on the moles of compounds of the formulae (I), (II), (III) and (IV) present in the polyhydroxy mixture. From about 10 or 20 mole percent to about 60 mole percent of the bis component is typical in the mixture.

The polyhydroxy mixture also contains a phenolic co-crosslinking composition having a hydroxyl functionality of two or more and may include any suitable phenolic components, such as resins obtained from the reaction of phenols or alkylated phenols with formaldehyde, such as novolac resins, resole resins, dicylcopentadiene phenol novolac; or other hydroxy functional polymeric resins, containing the residue of hydroxystyrene, for example. Suitable polyfunctional phenolic monomeric and/or oligomeric compounds include tris(hydroxyphenyl) methane; tris(hydroxyphenyl) ethane; 1,3,5-trihydroxybenzene; tetraphenolethane; 3,4,5-trihydroxybenzoic acid (also known as gallic acid) or its derivatives, or pyrogallol (also known as 1,2,3-trihydroxybenzol); or 1,2,4-trihydroxybenzol (also known as hydroxyhydrochinon); 1,8,9 trihydroxyanthracene (also known as dithranol or 1,8,9-anthracentriol), or 1,2,10-trihydroxyanthracene (also known s anthrarobine); 2,4,5-trihydroxypyrimidine; and mixtures and reaction products of these compounds. Still further phenolic components may be found in U.S. Patent Publication No. 2002/US01/19317, the disclosure of which is incorporated herein by reference. Monomeric, oligomeric and polymeric phenolic components may be blended if so desired to produce the phenolic co-crosslinking composition.

A preferred polyhydroxy co-crosslinking material is a novolac resin of the class including phenol formaldehyde resins, cresol formaldehyde resins and mixtures thereof. Perhaps the most preferred polyhydroxy novolac resins are those including the residues of a nitrogen heteroaryl compound, a phenol and an aldehyde, which resin may be selected from the group consisting of benzoguanamine phenol formaldehyde resins, acetoguanamine phenol formaldehyde resins, melamine phenol formaldehyde resins, benzoguanamine cresol formaldehyde resins, acetoguanamine cresol formaldehyde resins, melamine cresol formaldehyde resins, and mixtures thereof. Many other reaction products between phenolics, nitrogen-containing heteroaryl compounds, and an aldehyde would be recognized as forming suitable hydroxy-containing resins by one skilled in the art.

In yet other aspects, the invention includes a curable epoxy composition comprising:

an epoxy resin;
a co-crosslinking polyhydroxy mixture including:
a mixture of phosphine oxides including hydroxyaryl phosphine oxides of the formulae:
a mono(hydroxyaryl)phosphine oxide of the formula:

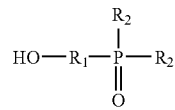
(I)

wherein $R_1$ is a divalent, substituted or unsubstituted arylene moiety and $R_2$ is a monovalent, substituted or unsubstituted aryl moiety or is an alkyl 15 moiety or is an aralkyl moiety; and
a bis(hydroxyaryl)phosphine oxide of the formula:

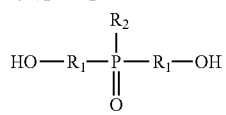
(II)

wherein $R_1$ and $R_2$ are defined as above; and
a tris(hydroxyaryl)phosphine oxide of the formula:

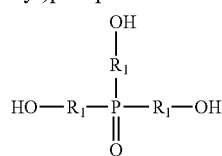
(III)

wherein $R_1$ is defined as above; and
optionally containing minor amounts of a pentavalent phosphine oxide of the formula:

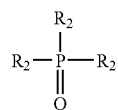
(IV)

wherein $R_2$ is defined as above and the polyhydroxy mixture further includes a phenolic co-crosslinking composition including a phenolic component having a hydroxy functionality of two or more as noted above.

The epoxy resin is in some embodiments a novolac epoxy resin while in other embodiments the epoxy resin may be based on epichlorohydrin and bisphenol A or in still yet other embodiments the epoxy resin is based on epichlorohydrin and bisphenol F. The curable epoxy compositions preferably have a phosphorous content of from about 0.2 wt. percent to about 5 wt. percent with from about 1 wt. percent to about 4 wt. percent being somewhat typical. From about 2 wt. percent to about 3 wt. percent is particularly preferred. Generally, the polyhydroxy mixture has a total hydroxy content of from about 50 mole % to about 150 mole % of the stoichiometric amount required to cure the epoxy resin present, with a hydroxy content of from about 75 mole % to about 125 mole % of the stoichiometric amount required to cure the epoxy resin being more preferred in many cases. Still more preferred may be a hydroxy content of from about 85 mole % to about 110 mole % of the stoichiometric amount required to cure the epoxy resin.

In many embodiments, from 1 mole % to about 99 mole % of the hydroxy moieties in the curing agent mixture are novolac resin hydroxyl groups whereas from about 25 mole % to about 75 mole % of the hydroxy moieties in the mixture being novolac resin hydroxyl groups is typical. Also, anywhere from about 1 mole % to about 99 mole % of the hydroxy moieties in the mixture are phosphine oxide hydroxyaryl moieties whereas from about 25 mole % to about 75 mole % of the hydroxy moieties in the mixture being phosphine oxide hydroxyaryl moieties is typical.

In still yet another aspect of the invention, there is provided a resin-impregnated composite comprising a reinforcing component and the flame retardant epoxy composition described herein, at least partially cured. The composite includes a glass filler, a glass fiber or a glass fabric and optionally includes a copper foil layer adhered to the resin-impregnated composite. Such laminates generally include a plurality of layers of resin-impregnated glass fabric, press-formed into a substantially integrated structure generally inseparable into its constituent layers.

Still yet further aspects of the invention will become apparent from the discussion which follows.

BRIEF DESCRIPTION OF DRAWINGS

The invention is described in detail below with reference to the drawings wherein like numerals designate similar parts and the invention is described in connection with numerous examples. In the drawings.

DETAILED DESCRIPTION OF THE INVENTION

Figure 1:
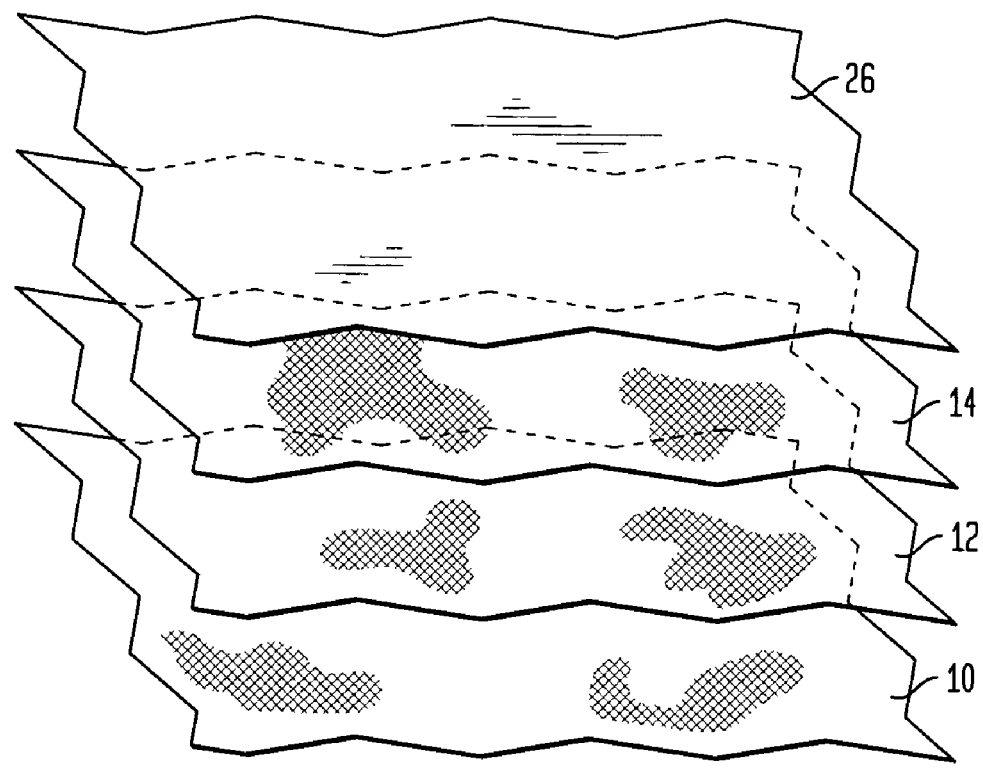
FIG. 1 is a perspective exploded schematic view showing a plurality of resin-impregnated glass cloth layers and a copper foil layer of the class used to make printed wiring boards.

This invention pertains to the use of hydroxylated phosphine oxides described herein blended with a polyhydroxy co-curing agent in epoxy resin formulations. A typical curable formulation is comprised of, but not limited to, A) a hydroxylated phosphine oxide mixture of the present invention, B) a novolac resin of the present invention, C) an epoxy resin or epoxy resin combination, D) a filler or filler combination, E) curing accelerator, F) and a suitable solvent or solvent combinations. This formulation may also contain additives or reactives chosen by one skilled in the art to effect certain desired properties.

A preferred embodiment of this invention is the use of the hydroxylated phosphine oxides as a blend with polyhydroxy novolac resins. The hydroxylated phosphine oxides described herein are easily dissolved as a mixture with a wide variety of novolac resins with the use of a suitable solvent. These resin solutions provide a resin curing solution that imparts excellent handling and ease of use. These resin curing solutions are stable and inhibit crystallization of either the phosphine oxide or the selected novolac. Alternatively, the blend may be formed in selected cases by melt blending the phosphine oxide with a suitable novolac. If the novolac resin is a solid, the hydroxyarylphosphine oxide/novolac resin mixture may be processed as a solid blend and used in the solid form. An optional embodiment is the addition of the hydroxylated phosphine oxide and the novolac resin individually into the curable resin formulation.

Unless otherwise indicated, or it is clear from the context, the terminology phenolic novolac resin and the like means and includes hydroxyl-functional resinous compositions including the condensation products of one or more substituted or unsubstituted phenolic compounds and one or more aldehydes, preferably formaldehyde. Such resins may optionally include heteroaryl components such as melamine and guanamines as noted hereinafter.

In one of the embodiments of this invention, $R_1$ in the above formulae is derived from an alkyl aryl ether. Examples of such starting materials include methoxyphenyl-, 4-methoxynaphthyl-, o-methoxycresyl- and so forth.

This invention utilizes a mixed Grignard reagent system to produce a mixture of phosphine oxides. This invention can be applied to a wide array of compounds wherein an arylmagnesium halide can be mixed with an alkoxyarylmagnesium halide and reacted with phosphorus oxychloride, or alternatively, an alkylmagnesium halide can be reacted with phosphorus oxychloride in tandem with an alkoxyarylmagnesium halide. The generalized approach is to use a main Grignard reagent that contains a functional group that can be chemically transformed to a group capable of reacting with a wide variety of active intermediates, and furthermore, using a second Grignard reagent that is functionally inert. The relative stoichiometry between the two Grignard reagents and the phosphorus oxychloride can be adjusted to affect the distribution of the mixtures in the desired fashion at will. The two Grignard reagents can be premixed and reacted with the phosphorus oxychloride together, or the reagents can be added to the phosphorus oxychloride in a serial fashion, depending on the requirements of the particular reaction. Alternatively, phosphorus trichloride can be used in place of phosphorus oxychloride in the reaction, followed by oxidizing the resulting phosphine to phosphine oxide by standard synthetic procedures.

Alternatively, a wide array of organometallic reagents and intermediates can be used to effect the product mixture distribution in place of the magnesium approach. These reagents are, for example, but not limited to: organozincs, -sodium, -lithium, -potassium, and transition metal facilitated routes in general, which are known to one skilled in the art.

The invention pertains, with regards to the hydroxylated phosphine oxide component, in a preferred aspect, to the substances obtained by a two-step process. The first step involves the reaction of phosphorus oxychloride with a novel mixture of phenylmagnesium bromide and 4-methoxyphenylmagnesium bromide. The reaction produces a further novel mixture of four products; triphenylphosphine oxide, diphenyl(4-methoxyphenyl)phosphine oxide, di(4-methoxyphenyl)phenylphosphine oxide, and tri(4-methoxyphenyl)phosphine oxide. This product mixture can then be reacted with concentrated hydrobromic acid in the presence of a catalytic amount of a metal halide to produce the corresponding mixture of free phenols: triphenylphosphine oxide, diphenyl(4-hydroxyphenyl)phosphine oxide, di(4-hydroxyphenyl)phenylphosphine oxide, and tri(4-hydroxyphenyl)phosphine oxide. Additionally, the neutral material could be removed by washing techniques if so desired.

In addition, the unsubstituted phenyl group in the product, as described above in the preferred aspect, for example, can be replaced by substituting bromobenzene or chlorobenzene with another aryl or alkyl halide. Examples of aryl halides include, but are not limited to 1-bromonapthylene; 2-bromonaphthylene; 4-bromotoluene; 4-bromophenoxybenzene; and 5-bromo-1,2,4-trimethylbenzene. Examples of alkyl halides include, but are not limited to, methyl bromide and tert-butyl bromide. The reactive groups for the final product mixture, in the most preferred case, would be the hydroxyl group, which is capable of reacting with epoxy resins in the co-cure with the novolac resins, or as a curing agent directly.

The curable, flame retardant epoxy resin compositions suitable for use in the manufacture of prepregs, and laminates can be prepared from the formulation of hydroxyaryl phosphine oxides with novolac resins and a commercially available epoxy resin. The product distribution of the hydroxyaryl phosphine oxide mixture enables certain physical characteristics to be easily affected in the cured and uncured resin. The properties involved are, for example, but not limited to, molecular weight, viscosity, glass transition temperature, and gel point. The reasons for this are related to the type and source of aromatic hydroxyl groups present in the curing agent mixture. The hydroxyaryl phosphine oxide mixtures that contain a higher content of the tris analog will exhibit a higher glass transition temperature. The co-curing agent mixture that contains a higher percentage of novolac resin will exhibit a gel point at a lower % conversion. This provides a processing benefit of a longer C-stage window relative to using the straight hydroxy aryl phosphine oxide curing agent alone (Table 1).

The epoxy resin can be crosslinked with a combination of the mixture of hydroxyarylphosphine oxides of formulae (I), (II) and (III), and optionally the pentavalent phosphine oxide of formula (IV), along with a phenolic co-crosslinking composition. The phenolic co-crosslinking composition comprises novolac resins such as phenol-formaldehyde resins, cresol-formaldehyde resins, and mixtures thereof. A polymer of a phenol, nitrogen heteroaryl compound and aldehyde is also suitable. Examples include benzoguanamine-phenol-formaldehyde resins, acetoguanamine-phenol-formaldehyde resins, melamine-phenol-formaldehyde resins, benzoguanamine-cresol-formaldehyde resins, acetoguanamine-cresol-formaldehyde resins, melamine-cresol-formaldehyde resins, and mixtures thereof.

The co-curing composition also includes a phenolic material with hydroxy functionality of two or more. Typical phenolic compounds are:

a) Resins obtained from the reaction of phenols or alkylated phenols with formaldehyde, such as novolac resins or resole resins.

b) Polyhydroxy aromatic materials such as: tris(hydroxyphenyl)methane; tris(hydroxyphenyl)ethane; 1,3,5-trihydroxybenzene; tetraphenolethane, and so forth as noted above.

The preferred phenolic co-curing component is a novolac resin of the class including phenol formaldehyde resins, cresol formaldehyde resins and mixtures thereof. Preferred polyhydroxy novolac resins include the residue of a nitrogen heteroaryl compound, a phenol and an aldehyde, which may be selected from the group consisting of benzoguanamine phenol formaldehyde, acetoguanamine phenol formaldehyde, melamine phenol formaldehyde, benzoguanamine cresol formaldehyde, acetoguanamine cresol formaldehyde, melamine cresol formaldehyde, and mixtures thereof. Many other reaction products between phenolics, nitrogen-containing heteroaryl compounds, and an aldehyde would be recognized as forming suitable hydroxy-containing resins by one skilled in the art.

Polyhydroxy novolac resins that contain phenol/aldehyde copolymers such as copolymers containing the residue of formaldehyde and one or more of phenol or a substituted phenol such as cresol or bisphenol A, or various other hydroxy-substituted benzenes, are particularly preferred in some embodiments. This component is used as a co-hardener with the stated hydroxylated phosphine oxides of this invention. Phenol novolac resins are readily available commercial materials and are typically characterized by the following general chemical structure:

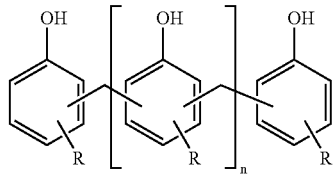

(V)

where R may represent hydrogen, an alkyl group such as methyl and so forth.

Suitable novolac resins include, for example, but are not limited to: Durite® SD-1708, SL-1710, SD-1502, SD-1702, SD-1731, SD-1734, SD-241A, SD-423A, RD-2414, SD-5132, SD-7280, SD-1502, SD-500C, available from the Borden Chemical Company; GP-2074, 5300, 5833, 834D54, available from Georgia Pacific; HRJ-11040, 1166, 1583, 2210, 2355, 2901, CRJ-406, and FRJ-425/200, available from Schenectady International.

Polyhydroxy novolac resins that include a copolymer comprising a reaction product of a nitrogen heteroaryl compound, a phenol and an aldehyde are particularly preferred in some cases. As previously noted, these resins may be selected from the group consisting of benzoguanamine phenol formaldehyde, acetoguanamine phenol formaldehyde, melamine phenol formaldehyde, benzoguanamine cresol formaldehyde, acetoguanamine cresol formaldehyde, melamine cresol formaldehyde, and mixtures thereof. Many other reaction products between phenolics, nitrogen-containing heteroaryl compounds, and an aldehyde would be recognized as forming suitable hydroxy-containing resins by one skilled in the art. If so desired, other aldehydes and/or other triazine compounds may be used. These resins are prepared as disclosed in Encyclopedia of Polymer Science and Engineering, $2^{nd}$ ed., Vol 11, p 50; or in Kirk-Othmer Encyclopedia of Chemical Technology, $4^{th}$ ed. Vol 18, p 606.

Representative epoxy resins suitable for use in the present invention are presented in *Epoxy Resins Chemistry and Technology, Second Edition* edited by Clayton A. May (Marcel Dekker, Inc. New York, 1988), *Chemistry and Technology of Epoxy Resins* edited by B. Ellis (Blackie Academic & Professional, Glasgow, 1993), *Handbook of Epoxy Resins* by H. E. Lee and K. Neville (McGraw Hill, New York, 1967), and EP 1116774 A2. Suitable epoxy resins are, but not limited to, epoxy resins based on bisphenols and polyphenols, such as, bisphenol A, tetramethylbisphenol A, bisphenol F, bisphenol S, tetrakisphenylolethane, resorcinol, 4,4'-biphenyl, dihydroxynaphthylene, and epoxy resins derived from novolacs, such as, phenol:formaldehyde novolac, cresol:formaldehyde novolac, bisphenol A novolac, biphenyl-, toluene-, xylene, or mesitylene-modified phenol:formaldehyde novolac, aminotriazine novolac resins and heterocyclic epoxy resins derived from p-amino phenol and cyanuric acid. Additionally, aliphatic epoxy resins derived from 1,4-butanediol, glycerol, and dicyclopentadiene skeletons, are suitable, for example. Many other suitable epoxy resin systems are available and would also be recognized as being suitable by one skilled in the art.

It is generally advantageous to use an epoxy resin which possesses on average more than 1 and preferably at least 1.8, more preferably at least 2 epoxy groups per molecule. In the most preferred case the epoxy resin is a novolac epoxy resin with at least 2,5 epoxy groups per molecule. In the broadest aspect of the invention, the epoxy resin may be any saturated or unsaturated aliphatic, cycloaliphatic, aromatic or heterocyclic compound which possesses more than one 1,2-epoxy group. Examples of heterocyclic epoxy compounds are diglycidylhydantoin or triglycidyl isocyanurate (TGIC).

The epoxy resin is preferably one that has no lower alkyl aliphatic substituents, for example the glycidyl ether of a phenol novolac, or the glycidyl ether of bisphenol-F. Preferred epoxy resins are epoxy novolac resins (sometimes referred to as epoxidized phenolic novolac resins, a term which is intended to embrace both epoxy phenol novolac resins and epoxy cresol novolac resins).

Epoxy novolac resins (including epoxy cresol novolac resins) are readily commercially available, for example, under the trade names D.E.N.™, Quatrex™, (Trademarks of the Dow Chemical Company), and Epon™ (trademark of Resolution Performance Products). The materials of commerce generally comprise mixtures of various glycidoxyphenyl and methyl-, ethyl- propyl- glycidoxyphenyl groups.

The arylalkyletherphosphine oxide mixtures or the corresponding hydroxyaryl-phosphine oxide mixtures can optionally be applied for use as flame retardants for a vast array of thermosetting and thermoplastic resins, such as polycarbonates, polyesters, vinyl esters, cyanate esters, polyamides, polyimides, polyurethanes, and many others; but more specifically, to the flame retardation of epoxy resins as a general approach. In addition, the deprotection of alkylaryl ethers in the synthesis generates an alkyl halide, which is a value-added product.

The phosphine oxide mixtures, containing hydroxy substituents, may be converted to any number of functional groups by those skilled in the art, such as, but not limited to, ethers, carbonates, carbamates, and esters to modify the properties of the materials to improve the compatibility in a given resin system. In particular, these mixtures may be used directly as a cross-linking agent in epoxy resin formulations. The hydroxyphenyl mixtures are intended for flame retardant printed wiring boards. In addition, the resins described in the present invention may be formulated with additional additives and fillers to affect cure rate, enhance flame retardancy, and increase physical properties.

Additionally, the compositions of the present invention may be formulated with other flame-retardant materials as co-additives with the compositions of the present invention to improve the performance. These co-FR materials could be either inorganic or organic and can be reactive or additive based compounds. Examples of inorganic additive type materials include, but not limited to, alumina trihydrate (ATH), magnesium hydroxide, barium hydroxide, calcium carbonate, titanium dioxide, and silicon dioxide. A particularly useful co-FR filler material is ATH. The self-extinguishing nature of the co-curing agent of the present invention is further enhanced to meet the UL-94 V-0 requirement by the addition of ATH (Table 3). Other filler materials described above would be recognized as being beneficial to the flame-retardant properties by one skilled in the art. Examples of organic based additives or reactives include, but are not limited to, triphenyl phosphate, resorcinol bis (di-2,6-xylyl phosphate), 9,10-dihydro-9-oxa-10-phosphaphenanthrene-10-oxide, bisphenol A bis(diphenyl-phosphate), melamine, melamine phosphate, melamine borate and many others familiar to one skilled in the art.

Fillers may be used in the invention to affect physical properties and to reduce costs. Typically, fillers and reinforcing agents include mica, talc, kaolin, bentonite, wollastonite, glass fiber, glass fabrics glass matt, milled glass fiber, glass beads (solid or hollow), silica, or silicon carbide whiskers and so forth. Many of these materials are enumerated in the *Encyclopedia of Materials Science and Engineering*, Vol. # 3, pp. 1745–1759, MIT Press, Cambridge, Mass. (1986), the disclosure of which is incorporated herein by reference. Combinations of fillers are preferred in some embodiments; whereas in other embodiments, the reinforcing agent makes up most of the composite of the invention, as in the case of glass fabric used in prepregs and laminates for printed wiring boards.

Suitable curing accelerators or catalysts that can be used in the formulation include, but are not limited to, substituted or unsubstituted imidazoles such as imidazole, 2-methylimidazole, 2-ethyl-4-methylimidazole, 2-phenylimidazole, etc. Other catalysts include tertiary amines and amides. Phosphine catalyst can also be used, such as triphenylphosphine. Lewis acids may also be used alone or in combination with other catalysts, which is a common practice to one skilled in the art. Typical examples of Lewis acids include oxides and hydroxides of zinc, tin, silicon, aluminum, boron, and iron; borontrifluoride or boric acid can also be used.

In accordance with the practice of this invention a resin-impregnated composite comprising at least one of a filler or reinforcing agent and the curable composition as described herein is provided, which is at least partially cured. For example, the hydroxyaryl mixtures, polyhydroxy resins and epoxy resins of the invention are advantageously used in the fabrication of prepregs and laminates used to make printed wiring boards. The resin prepared as described herein is mixed with one or more hardener(s) and optionally accelerator(s) and applied to a glass cloth, such as glass cloth layers 10, 12, 14 as shown in FIG. 1. The resin-impregnated sheets or prepregs are then at least partially cured in an oven typically at 150° C.–200° C. for a few minutes; for example, from 1–5 minutes.

Figure 2:
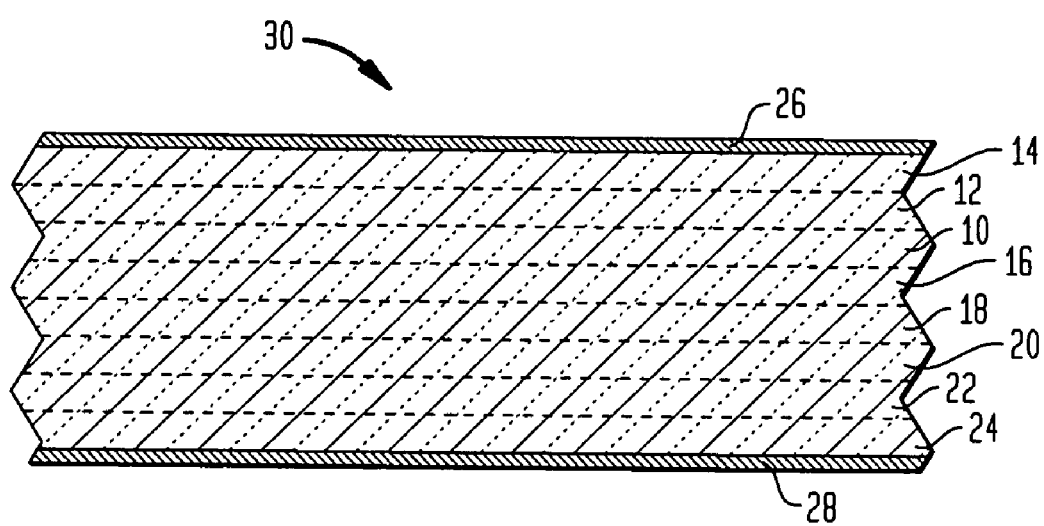
FIG. 2 is a schematic view in sectional elevation of a heat-pressed copper clad laminate of the class used to make printed wiring boards including a plurality of intermediate strata formed from glass prepregs which have been heat-cured into a substantially integrated structure generally inseparable into its constituent layers.

In order to prepare a laminate of the class used for printed wiring boards, a plurality of prepregs are stacked next to each other as shown in FIG. 2, wherein resin-impregnated layers 10–24 are shown. On each side of the stack there is provided a copper foil layer, such as layers 26, 28. The stack, including cloth layers 10–24 and foil layers 26, 28, is then pressed at elevated temperatures in a press for an hour or more to produce a consolidated laminate 30. Laminate 30 thus includes a plurality of fused layers 10–24 of the resin-impregnated glass fabric. If so desired, more or fewer layers of prepregs or foil may be used depending on the desired structure.

EXAMPLES

In the Examples that follow, the following abbreviations are used:

| | |
|---|---|
| ATH | alumina trihydrate |
| CDCl$_3$ | deutero-chloroform |
| DEN 438 | epoxidized novolac resin available from the Dow Chemical Co. |
| d$_6$-DMSO | d$_6$-dimethylsulfoxide |
| Dowanol PM | 1-methoxy-2-propanol |
| DSC | differential scanning calorimetry |
| Epon 164 | epoxidized cresol novolac resin available from Resolution Performance Products |
| FR | flame retardant |
| GC | gas chromatograph |
| LC | liquid chromatograph |
| MeCN | acetonitrile |
| 2MI | 2-methylimidazole |
| MW | molecular weight |
| NMR | nuclear magnetic resonance spectroscopy, usually of phosphorus, $^{31}$P |
| POCl$_3$ | phosphorus oxychloride |
| PWB | printed wiring boards |
| rt | room temperature |
| T$_g$ | glass transition temperature |
| SD-1708 | phenol-formaldehyde resin (novolac resin) available from Borden Chemical Co. |
| TGA | thermal gravimetric analysis |
| THF | tetrahydrofuran |
| TPPO | triphenylphosphine oxide |

EXAMPLES

Example 1a

Preparation of
Bis(4-methoxyphenyl)Phenylphosphine Oxide
Mixture

Magnesium (1430 g, 58.8 mol), tetrahydrofuran (12 L), and 1,2-dibromoethane (2.2 g, 0.012 mol) were stirred under nitrogen for 1 h. The mixture was then heated to reflux and then the heating stopped. Bromobenzene (3000 g, 19.1 mol) and 4-bromoanisole (7150 g, 38.2 mol) were added consecutively at a rate to maintain a slow reflux (67° C.) over a period of 4 h. The reaction mixture was then held for a further 5 h at 70° C. Phosphorus oxychloride (2930 g, 19.1 mol) was added at a rate to maintain a temperature of 70° C. (5 h). The reaction was then held at 70° C. for a further 5 h. The reaction mixture was quenched and worked up to give the product mixture (5772 g, 89%) as an amber colored oil. $^{31}$p NMR: (d$_6$-DMSO) δ 26.9 (s, 6%), 26.8 (s, 23%), 26.6 (s, 44%), 26.5 (s, 27%). GC (area %): triphenylphosphine oxide 3.8%, diphenyl(4-methoxyphenyl)phosphine oxide 21.5%, bis(4-methoxyphenyl)phenylphosphine oxide 40.6%, and tris(4-methoxyphenyl)phosphine oxide 25.7%.

Example 1b

Preparation of
Bis(4-hydroxyphenyl)Phenylphosphine Oxide
Mixture

Bis(4-methoxyphenyl)phenylphosphine oxide mixture (2359 g, 6.97 mol), hydrobromic acid (48%, 8344 g, 49.5 mol), and potassium bromide (243 g, 2.04 mol) were stirred at 120° C. for 48 h. The flask was fitted with a sodium sulfite scrubber for containment of methyl bromide. The lower aqueous layer was removed and the product layer was worked up to afford bis(4-hydroxyphenyl)phenylphosphine oxide mixture (Composition VI) as a tan powder (1601 g, 74%). m.p. (DSC): 93° C. $^{31}$P NMR (d$_6$-DMSO): δ 27.7 (s, 24.7%); 27.5 (s, 47.7%); 27.4 (s, 25.4%); 27.2 (s, 2.2%).

Example 1c

Preparation of Benzoguanamine-modified Phenol-Formaldehyde Novolac Resin

This material was prepared based on patent application EP 0 795 570 A1 (Toshiba) example A. Formalin (1026g, 13.2 mol) was added over 0.5 h to a solution of phenol (1500 g, 15.9 mol), benzoguanamine (180 g, 0.96 mol), and oxalic acid (30.2 g, 0.24 mol) at 90–95° C. The mixture was then held at 95° C. for 3 h. The reaction mixture was then vacuum stripped to remove water and excess phenol under reduced pressure to 30 Torr and 165° C., and held at temperature and pressure for 30 minutes. 2-Butanone (540 g) was then added to the molten amber product (998 g, Resin VII) to give a solution at approximately 65% resin solids. GPC (polystyrene): Mw, 940; Mn, 570; pd, 1.68. % solids: 68%, free phenol: not detected by HPLC.

Example 1d

Preparation of Tris(4-methoxyphenyl)Phosphine Oxide

A reaction flask under nitrogen containing magnesium turnings (223.9 g, 9.21 mol) and 1950 mL THF was charged with 1 drop of 1,2-dibromoethane and heated to reflux for 1 h. Heating was removed and p-bromoanisole (1683 g, 9.00 mol) was added dropwise at a rate to maintain reflux. After holding the reaction mixture overnight, POCl$_3$ (460.0 g, 3.00 mol) was added slowly over 2 h at 50–79° C. and the resulting mixture was held overnight at 50° C. The product was isolated by aqueous workup to give 984.5 g of tris(4-methoxyphenyl)phosphine oxide (89.0% yield). Recrystallized analytical specimen (from ethyl acetate): mp 145.2° C. (DSC), lit. 143–144° C. (*J. Org. Chem.* 1960, 25, 2001).

Example 1e

Preparation of Tris(4-hydroxyphenyl)phosphine Oxide

A reaction flask containing tris(4-methoxyphenyl)phosphine oxide (973.2 g) was charged with 48% aq HBr (2250 mL) and KBr (126.1 g). The flask was fitted with a sodium sulfite scrubber for containment of methyl bromide. The reaction mixture was heated to reflux (114° C.) and maintained at reflux until complete based on HPLC analysis. The product (Compound VIII) was worked up to give 558.5 g of tris(4-hydroxyphenyl)phosphine oxide ($^{31}$P NMR (d$_6$-DMSO): δ 27.6 (s); $^1$H NMR (d$_6$-DMSO): δ 10.9 (s, 3H), 7.38 (m, 6H), 6.84 (m, 6H)).

Example 2

Gel and Thermal Properties of Co-curing System

Formulations were prepared on small scale using DEN 438 epoxy resin with 2-MI catalyst and different curing agent combinations as depicted in Table 1. The mole ratios were kept constant. The gel point was determined at 170° C. according to IPC Test Method IPC-TM-650-2.3.18. The gelled material was divided into two pieces. One piece was tested by DSC and the other piece was post-cured in an oven at 200° C. overnight. The DSC scans show that the amount of reactivity left after reaching the gel point in the straight novolac cure is quite high (181 J/g) compared with the cases where Composition VI is used, indicating that the extent of conversion of the Composition VI reactions is much further at the gel point. The resulting cured resin has a lower Tg temperature when curing with Composition VI only, a characteristic that is modified when using the co-curing agent approach.

TABLE 1

Comparsion of Gel and Thermal Properties of Different Curing Approaches.

| Varnish Components | Formulation No. (phr) | | |
|---|---|---|---|
| | 1 | 2 | 3 |
| DEN 438 | 100 | 100 | 100 |
| Composition VI | 79 | 0 | 51.2 |
| SD1708 | 0 | 62 | 18.8 |
| 2-MI | 0.05 | 0.05 | 0.05 |
| Reactivity/Properties | | | |
| Gel Time @ 170° C. (sec) | 210 | 265 | 215 |
| ΔH (DSC, J/g)$^{(a)}$ | 96 | 181 | 117 |
| Exo Peak (DSC, ° C.)$^{(a)}$ | 183 | 191 | 178 |
| Tg (DSC, ° C.)$^{(b)}$ | 151 | 181 | 161 |
| % P | 4.4 | 0 | 3.0 |
| OH/Epoxy Eq ratio | 0.9 | 0.9 | 0.9 |

$^{(a)}$DSC of gelled material
$^{(b)}$DSC of gelled material after overnight post cure at 200° C.

Example 3

Comparison of Various Curing Agent Systems

A sample of a phosphine oxide mixture VI from example 1b was mixed with the phenolic novolac resin SD-1708 and dissolved in Dowanol PM. This solution was added to the DEN 438 epoxy resin along with 2MI catalyst to form a varnish solution. Additional solvent was added as needed to achieve the desired resin viscosity. The varnish was coated onto eight plies of 7628 glass fabric, B-staged at 170° C., stacked and pressed at 190° C. to give a laminate board. This procedure was repeated for the systems depicted in Table 2.

The intrinsic flame-retardant ability is shown for each laminate by comparing the UL-94 burn times. When using the hydroxyaryl phosphine oxide/phenolic novolac co-curing agent system, the same level of flame retardancy was achieved as when using Composition VI as the sole curing agent, but at a reduced phosphorus level and with an improved glass transition temperature.

TABLE 2

DEN 438 Epoxy Resin Cured with Different Curing Agent Systems.

| Formulation | | | Cured Resin | Laminate$^{(a)}$ UL-94 | | |
|---|---|---|---|---|---|---|
| Sample | | | Tg, ° C. | Ave. Burn times (s) | | |
| No. | Curing Agent System | % P | (DSC) | T1 | T2 | Total |
| 1 | Composition VI | 4.1 | 129 | 3 | 19 | 112 |
| 2 | SD-1708 | 0.0 | 168 | —$^{(b)}$ | — | — |

TABLE 2-continued

DEN 438 Epoxy Resin Cured with Different Curing Agent Systems.

| Sample No. | Formulation Curing Agent System | % P | Cured Resin Tg, °C. (DSC) | Laminate[a] UL-94 Ave. Burn times (s) T1 | T2 | Total |
|---|---|---|---|---|---|---|
| 3 | Composition VI/SD-1708 mixture | 3.0 | 164 | 6 | 15 | 83 |

[a] 8-ply laminate using 7628 glass, 5 test coupons each. Coupons were self-extinguishing unless noted.
[b] The sample burned to the clamp.

A separate experiment was conducted by using Compound VIII and SD-1708 novolac resin as the co-curing agent with DEN 438 epoxy resin to give a system containing 3.0% P. The resulting cured resin had a Tg (DSC) of 184° C.

Example 4

Laminates Using Co-curing Agent System with ATH

The procedure of Example 3 was followed, but ATH was added to the formulation (Table 3). The laminates were tested for flame retardancy according to the UL-94 test.

TABLE 3

Co-curing Agent Formulations Using ~30% ATH on Organics.

| | Formulation No. | | | |
|---|---|---|---|---|
| | 4 | 5 | 6 | 7 |
| DEN 438 | 100 | 100 | 0 | 100 |
| Epon 164 | 0 | 0 | 100 | 0 |
| Composition VI | 0 | 55 | 48.5 | 52.2 |
| SD-1708 | 62 | 25 | 10.4 | 0 |
| Resin VII | 0 | 0 | 0 | 21.8 |
| 2MI | 0.10 | 0.06 | 0.07 | 0.001 |
| ATH | 44 | 54 | 48 | 52.2 |

TABLE 3-continued

Co-curing Agent Formulations Using ~30% ATH on Organics.

| | Formulation No. | | | |
|---|---|---|---|---|
| | 4 | 5 | 6 | 7 |
| Physical Properties | | | | |
| Formulation Organics % P | 0 | 3.0 | 3.0 | 3.0 |
| Cured Resin Tg, °C. (DSC) | 171 | 166 | 184 | 165 |
| Laminate UL-94 Burn Results | Fail | V-0 | V-0 | V-0 |
| Total Burn Time (5 coupons), sec. | 298 | 10 | 26 | 5 |

The formulation using straight novolac curing (No. 4) failed the UL-94 burn test. Using Composition VI as a co-curing agent with the novolac resin SD-1708 or novolac resin VII allowed the laminates to pass the UL-94 test with a V-0 rating. The Tg was improved further when a cresol epoxy novolac (Epon 164) was used in place of DEN 438.

Additional Examples

Example 5

The mixed Grignard reaction was performed using varying stoichiometries of Grignard reagent (Table 4.). The product ratios were determined by use of $^{31}P$ NMR. The product distribution can be easily altered based on the final target physical properties needed.

TABLE 4

Mixed Grignard Reaction Using different Reagent Ratios.

| | PhMgBr | MeOPhMgBr | POCl₃ | | Mol % from $^{31}P$ NMR | | | |
|---|---|---|---|---|---|---|---|---|
| Entry | Equiv. | Equiv. | Equiv. | % Yld. | TPPO[1] | Mono[2] | Bis[3] | Tris[4] |
| 1 | 0.60 | 2.4 | 1 | 85 | 0 | 9.7 | 38.3 | 52.0 |
| 2 | 1.0 | 2.0 | 1 | 89 | 6 | 23 | 44 | 27 |
| 3 | 1.5 | 1.5 | 1 | 80 | 12.1 | 37.2 | 37.5 | 13.2 |

[1] triphenylphosphine oxide.
[2] diphenyl(4-methoxyphenyl)phosphine oxide
[3] bis(4-methoxyphenyl)phenylphosphine oxide
[4] tris(4-methoxyphenyl)phosphine oxide.

Example 6a

Bis(4-methoxyphenyl)(4-methylphenyl)phosphine Oxide Mixture

Magnesium (1430 g, 58.8 mol), tetrahydrofuran (12 L), and 1,2-dibromoethane (2.2 g, 0.012 mol) were stirred under nitrogen for 1 h. The mixture was then heated to reflux and the heating stopped. A mixture of 4-bromotoluene (3268 g, 19.1 mol) and 4-bromoanisole (7150 g, 38.2 mol) was added at a rate to maintain a slow reflux (67° C.) over a period of 4 h. The reaction mixture was then held for a further 5 h at 70° C. Phosphorus oxychloride (2930 g, 19.1 mol) was added at a rate to maintain a temperature of 70° C. (5 h). The reaction was then held at 70° C. for a further 5h. The reaction mixture was then worked up to give the product mixture (5563.8 g, 83%) as an amber colored oil upon concentration. $^{31}$P NMR: ($d_6$-DMSO) δ 27.3 (s), 27.1 (s), 26.9 (s), 26.9 (s), 26.7 (s). GC(area %): tris(4-methylphenyl)phosphine oxide 3.8%, bis(4-methylphenyl)(4-methoxyphenyl)phosphine oxide 21.0%, bis(4-methoxyphenyl)(4-methylphenyl)phosphine oxide 39.4%, and tris(4-methoxyphenyl) phosphine oxide 25.1%.

Example 6b

Bis(4-hydroxyphenyl)(4-methylphenyl)Phosphine Oxide Mixture

A mixture of bis(4-methoxyphenyl)(4-methylphenyl) phosphine oxide mixture (470.2 g, 1.33 mol), hydrobromic acid (1458.1 g, 48%, 8.65 mol), and potassium bromide (45.0 g, 0.378 mol) were stirred for 112 h at 110° C. The flask was fitted with a sodium sulfite scrubber for containment of methyl bromide. The lower aqueous layer was removed and the molten product layer was worked up to give bis(4-hydroxyphenyl)-(4-methylphenyl)phosphine oxide mixture as a tan powder (292.8 g, 77% yield). m.p. (DSC): 142.5° C. $^{31}$P NMR ($d_6$-DMSO): 28.33 (s, 90.1%), 28.14 (s, 9.86%). LC(area %, THF:MeCN:water, 5:15:30): 16.2, 48.9, 20.1.

Example 6c

Bis(4-methoxyphenyl)-2,4,5-trimethylphenylphosphine Oxide Mixture

A reaction flask under nitrogen containing magnesium turnings (120 g, 4.94 mol) and 412 mL THF was charged with 0.5 g of 1,2-dibromoethane and heated to reflux for 1 h. A separate flask was charged with 5-bromo-1,2,4-trimethylbenzene (300 g, 1.51 mol), dissolved in 568 mL of THF. The heat was removed from the first flask and the 5-bromo-1,2,4-trimethylbenzene solution was added dropwise at a rate to maintain reflux. 4-Bromoanisole (536.7 g, 3.01 mol) was then added over 1.5 h at 75° C. reaction temperature. After holding the reaction mixture overnight, POCl$_3$ (231 g, 1.51 mol) was added dropwise at 40–80° C. The product mixture was isolated by aqueous workup to give 453.6 g (79% yield) of product mixture as a viscous liquid. The structure was consistent with NMR data.

Example 6d

Bis(4-hydroxyphenyl)-2,4,5-trimethylphenylphosphine Oxide Mixture

A reaction flask containing the bis(4-methoxyphenyl)-2,4,5-trimethylphenylphosphine oxide mixture (443.7 g) was charged with 48% aq. HBr (934 mL) and KBr (59.5 g). The flask was fitted with a sodium sulfite scrubber for containment of methyl bromide. The reaction mixture was heated to reflux (118° C.) and maintained at reflux until complete based on HPLC analysis. The molten product was worked up to give 283.3 g of bis(4-hydroxyphenyl)-2,4,5-trimethylphenylphosphine oxide mixture as a cream solid (68.9% yield). The ratio of products in the mixture based on $^{31}$P NMR was 39% tris(4-hydroxyphenyl)phosphine oxide, 49% bis(4-hydroxyphenyl)-2,4,5-trimethylphenylphosphine oxide, 11% di-2,4,5-trimethylphenyl-4-hydroxyphenylphosphine oxide, and 1% tris(2,4,5-trimethylphenyl)phosphine oxide.

Example 6e

Bis(4-methoxyphenyl)(1-naphthyl)phosphine Oxide Mixture

A mixture of magnesium (125.2 g, 5.15 mol), 1,2-dibromoethane (0.1 g, 0.5 mol) and dry THF (1 L) were stirred under a blanket of nitrogen at rt for 1 h. The mixture was brought to 65° C. and 1-bromonaphthalene (343.7 g, 1.66 mol) was added by drop. Once the reaction initiated, the heating was removed and the 1-bromonaphthalene addition was continued for 2 h at a rate to maintain 55° C. 4-Bromoanisole (623.5 g, 3.33 mol) was then added over 4 h. The temperature was adjusted to 65° C. and held for a further 3 h. Phosphorus oxychloride (255.5 g, 1.66 mol) was then added by drop to maintain a temperature of 50–60° C. over 6 hours. The temperature was then adjusted to 50° C. and held overnight. The reaction mixture worked up to afford bis(4-methoxy-phenyl)(1-naphthyl)phosphine oxide mixture as an amber solid (508 g, 79 yield %). $^{31}$P NMR (CDCl$_3$): δ 37.49 (s, 3.0%), 35.32 (s, 2.4%), 33.64 (s, 31.1%), 30.37 (s, 50.8%), 19.59 (s, 12.7%).

Example 6f

Bis(4-hydroxyphenyl)(1-naphthyl)Phosphine Oxide Mixture

Bis(4-methoxyphenyl)(1-naphthyl)phosphine oxide (352 g, 0.906 mol), hydrobromic acid (1474 g, 48%, 8.74 mol), and potassium bromide (45 g, 0.378 mol) were heated at 110° C. for 96 h. The flask was fitted with a sodium sulfite scrubber for containment of methyl bromide. The mixture was worked up to give the product as a brown solid (267 g, 82% yield). $^{31}$P NMR ($d_6$-DMSO): δ 35.19 (s, 5.2%), 30.96 (s, 74.4%), 27.16 (s, 19.3%). m.p. (DSC): 114.7° C.

Example 6g

Bis(4-methoxyphenyl)-tert-butylphosphine Oxide Mixture

Magnesium (30.1 g, 1.24 mol), tetrahydrofuran (400 mL), and 1,2-dibromoethane (1 drop) were stirred under nitrogen for 1 h. The mixture was then heated to reflux and the heating stopped. 4-Bromoanisole (224.4 g, 1.20 mol) was added as a mixture at a rate to maintain a slow reflux (67° C.) over a period of 4 h. The reaction mixture was then held for a further 3h at 70° C. To a tetrahydrofuran (500 mL) solution of phosphorus oxychloride (92.0g, 0.60 mol) was added by drop tert-butylmagnesium chloride (300 mL, 2.0 M, 0.60 mole) over 5.5 h and held at 40° C. for 1 h. Then the 4-methoxy-phenylmanesium bromide solution prepared above was added by drop over 2 h at a rate to maintain 40° C. The mixture was allowed to stir for 2 days at rt. The reaction mixture was worked up to yield a pale-yellow sticky solid (135.6 g, 71%). $^{31}$P NMR ($d_6$-DMSO): δ 44.7 (s, 43.0%), 37.8 (s, 7.0%), 26.5 (s, 7.6%), 25.4 (s, 36.4%), 14.9 (s, 6.0%).

Example 6h

Bis(4-hydroxyphenyl)-tert-butylphosphine Oxide Mixture

Bis(4-methoxyphenyl)-tert-butylphosphine oxide mixture (25.0 g), hydrobromic acid (770 g, 48%), and potassium bromide (30.0 g) were stirred for 25 h at 120° C. The flask was fitted with a sodium sulfite scrubber for containment of methyl bromide. The reaction mixture was worked up to give a tan solid (9.6 g, 40%). $^{31}$P NMR (d$_6$-DMSO): δ 46.3 (s, 31.8%), 39.6 (s, 31.7%), 28.7 (s, 20.4%), −8.2 (s, 16.1%).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A polyhydroxy mixture for co-crosslinking an epoxy resin and imparting flame resistance comprising,
   (a) a mixture of phosphine oxides including hydroxyaryl phosphine oxides of the formulae:
      (i) a mono(hydroxyaryl)phosphine oxide of the formula:

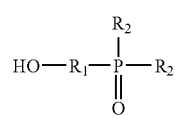

(I)

wherein $R_1$ is a divalent, substituted or unsubstituted arylene moiety and $R_2$ is a monovalent, substituted or unsubstituted aryl moiety or is an alkyl moiety or is an aralkyl moiety; and
      (ii) a bis(hydroxyaryl)phosphine oxide of the formula:

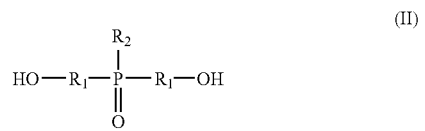

(II)

wherein $R_1$ and $R_2$ are defined as above; and
      (iii) a tris(hydroxyaryl)phosphine oxide of the formula:

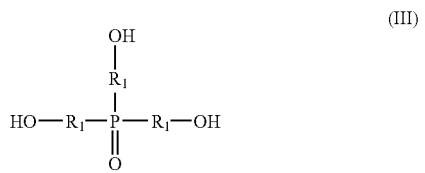

(III)

wherein $R_1$ is defined as above; and
      (iv) optionally containing minor amounts of a pentavalent phosphine oxide of the formula:

(IV)

wherein $R_2$ is defined as above; and
   (b) a phenolic co-crosslinking composition comprising a phenolic component having a hydroxy functionality of two or more.

2. The polyhydroxy mixture according to claim 1, wherein $R_1$ is derived from an alkyl aryl ether.

3. The polyhydroxy mixture according to claim 1, wherein the phosphine oxide mixture consists essentially of diphenyl(4-hydroxyphenyl)phosphine oxide, bis(4-hydroxyphenyl)phenylphosphine oxide and tris(4-hydroxyphenyl)phosphine oxide, optionally including minor amounts of triphenylphosphine oxide.

4. The polyhydroxy mixture according to claim 1, wherein the phosphine oxide mixture consists essentially of bis(4-methylphenyl)(4-hydroxyphenyl)phosphine oxide, bis(4-hydroxyphenyl)(4-methylphenyl)phosphine oxide and tris(4-hydroxyphenyl)phosphine oxide, said mixture optionally including minor amounts of tris(4-methylphenyl)phosphine oxide.

5. The polyhydroxy mixture according to claim 1, wherein the phosphine oxide mixture consists essentially of bis(1-naphthyl)(4-hydroxyphenyl)phosphine oxide, bis(4-hydroxyphenyl)(1-naphthyl)phosphine oxide and tris(4-hydroxyphenyl)-phosphine oxide, optionally including minor amounts of tris(1-naphthyl)-phosphine oxide.

6. The polyhydroxy mixture according to claim 1, wherein the phosphine oxide mixture consists essentially of bis(2-naphthyl)(4-hydroxyphenyl)phosphine oxide, bis(4-hydroxyphenyl)(2-naphthyl)phosphine oxide and tris(4-hydroxyphenyl)-phosphine oxide, optionally including minor amounts of tris(2-naphthyl)-phosphine oxide.

7. The polyhydroxy mixture according to claim 1, wherein the phosphine oxide mixture consists essentially of bis(4-phenoxyphenyl)(4-hydroxyphenyl)phosphine oxide, bis(4-hydroxyphenyl)(4-phenoxyphenyl)phosphine oxide and tris(4-hydroxyphenyl)phosphine oxide, optionally including minor amounts of tris(4-phenoxyphenyl)phosphine oxide.

8. The polyhydroxy mixture according to claim 1, wherein the phosphine oxide mixture consists essentially of bis(2,4,5-trimethylphenyl)(4-hydroxyphenyl)phosphine oxide, bis(4-hydroxyphenyl)(2,4,5-trimethylphenyl)phosphine oxide and tris(4-hydroxyphenyl)phosphine oxide, optionally including minor amounts of tris(2,4,5-trimethylphenyl)phosphine oxide.

9. The polyhydroxy mixture according to claim 1, wherein the phosphine oxide mixture consists essentially of bis(tert-butyl)(4-hydroxyphenyl)phosphine oxide, bis(4-hydroxyphenyl)(tert-butyl)phosphine oxide and tris(4-hydroxyphenyl)-phosphine oxide, optionally including minor amounts of tris(tert-butyl)phosphine oxide.

10. The polyhydroxy mixture according to claim 1, wherein said phosphine oxide mixture comprises from about 5 to about 40 mole percent of the mono(hydroxyaryl) phosphine oxide of the formula (I), from about 5 to about 60 mole percent of the bis(hydroxyaryl)phosphine oxide of the formula (II), from about 10 to 90 mole percent of the tris(hydroxyaryl)phosphine oxide of the formula (III) and from about 0 up to about 10 mole percent of the pentavalent phosphine oxide of the formula (IV), based on the moles of compounds of the formulae (I), (II), (III) and (IV) present in the polyhydroxy mixture.

11. The polyhydroxy mixture according to claim 1, wherein said phenolic co-crosslinking composition comprises a novolac resin.

12. The polyhydroxy mixture according to claim 11, wherein said phenolic co-crosslinking composition comprises a resin selected from the group consisting of phenol formaldehyde resins, cresol formaldehyde resins and mixtures thereof.

13. The polyhydroxy mixture according to claim 11, wherein said novolac resin is a polymer of a phenol, a nitrogen heteroaryl compound and an aldehyde.

14. The polyhydroxy mixture according to claim 13, wherein said novolac resin is selected from the group consisting of benzoguanamine phenol formaldehyde resins, acetoguanamine phenol formaldehyde resins, melamine phenol formaldehyde resins, benzoguanamine cresol formaldehyde resins, acetoguanamine cresol formaldehyde resins, melamine cresol formaldehyde resins, and mixtures thereof.

* * * * *